US011471059B2

(12) United States Patent
Watkins et al.

(10) Patent No.: US 11,471,059 B2
(45) Date of Patent: Oct. 18, 2022

(54) METHOD FOR EXPERT SYSTEM TO DYNAMICALLY ADAPT FITNESS TRAINING PLANS

(71) Applicant: Volt Athletics, Seattle, WA (US)

(72) Inventors: Trevor William Watkins, Seattle, WA (US); Daniel Roven Giuliani, Seattle, WA (US); Brian James McNaboe, Seattle, WA (US); Jace Atom Derwin, Mountlake Terrace, WA (US)

(73) Assignee: VOLT ATHLETICS, Seattle, WA (US)

( * ) Notice: Subject to any disclaimer, the term of this patent is extended or adjusted under 35 U.S.C. 154(b) by 411 days.

(21) Appl. No.: 16/813,386

(22) Filed: Mar. 9, 2020

(65) Prior Publication Data

US 2020/0281482 A1 Sep. 10, 2020

Related U.S. Application Data

(60) Provisional application No. 62/815,659, filed on Mar. 8, 2019.

(51) Int. Cl.
*G06F 3/048* (2013.01)
*A61B 5/02* (2006.01)
*G06N 20/00* (2019.01)
*G16H 20/30* (2018.01)

(52) U.S. Cl.
CPC ......... *A61B 5/02028* (2013.01); *G06N 20/00* (2019.01); *G16H 20/30* (2018.01)

(58) Field of Classification Search
CPC ..... A61B 5/02028; G16H 20/30; G06N 20/00
See application file for complete search history.

(56) References Cited

U.S. PATENT DOCUMENTS

| 5,007,283 | A | 4/1991 | Ambos |
| 5,966,676 | A | 10/1999 | Fujiwara et al. |
| 6,226,562 | B1 | 5/2001 | Philpott |
| 6,871,411 | B1 | 3/2005 | Kang et al. |
| 7,359,816 | B2 | 4/2008 | Kumar et al. |
| 9,057,636 | B2 | 6/2015 | Nagai |
| 9,797,765 | B2 | 10/2017 | Nagai |
| 10,831,645 | B1 * | 11/2020 | McNeil ............... G06F 11/3089 |
| 10,918,908 | B2 * | 2/2021 | Toivonen ............... G16H 40/67 |

(Continued)

*Primary Examiner* — David Phantana-angkool
(74) *Attorney, Agent, or Firm* — Rowan TELS LLC

(57) ABSTRACT

A method for an expert system to develop fitness training plans includes operating a dynamic exertion system to receive a rate of perceived exertion (RPE) through a user interface of a display device, combines the RPE with a movement, a movement load, and movement repetitions into movement set data, and operates a dynamic exertion algorithm. The method then displays an adjusted movement information display including the prescribed load and the prescribed movement repetitions through the user interface. The dynamic exertion algorithm generates a prescribed load and prescribed movement repetitions, determines a difference in RPE from the expected RPE through operation of a comparator, recalculates the one repetition maximum load value using the calibration and adjustment model when the difference in RPE is greater than an RPE threshold value, and generates a display control comprising the prescribed load and the prescribed movement repetitions.

18 Claims, 13 Drawing Sheets

DISPLAY DEVICE 802

(56) References Cited

U.S. PATENT DOCUMENTS

| | | |
|---|---|---|
| 11,325,004 B2 * | 5/2022 | Yi ........................ A61B 5/1125 |
| 2008/0228336 A1 | 9/2008 | Spranger |
| 2013/0041270 A1 | 2/2013 | Chang |
| 2014/0320110 A1 | 10/2014 | Matsui et al. |
| 2017/0266499 A1 * | 9/2017 | Sanders .................... G06N 3/04 |
| 2019/0183430 A1 * | 6/2019 | Alphonse .............. A61B 5/1118 |
| 2020/0269123 A1 * | 8/2020 | Sachs ................. A63B 71/0622 |
| 2020/0281482 A1 * | 9/2020 | Watkins ............. A61B 5/02028 |
| 2022/0044807 A1 * | 2/2022 | Sanders ................. A41D 1/002 |

* cited by examiner

1202

1204

METHOD FOR EXPERT SYSTEM TO DYNAMICALLY ADAPT FITNESS TRAINING PLANS

CROSS-REFERENCE TO RELATED APPLICATIONS

This application claims the benefit of U.S. provisional patent application Ser. No. 62/815,659, filed on Mar. 8, 2019, the contents of which are incorporated herein by reference in their entirety.

BACKGROUND

For a variety of reasons, exercisers often do not have an accurate understanding of their strength and loading capabilities for a given exercise, such as bench press. Currently, many fully automated systems do not prescribe any loading in the case where an expected one repetition maximum (1RM) is unknown. This is an issue because exercisers have difficulty determining the correct loading for each set, which is detrimental to the integrity of the training and the user experience. Therefore, a need exists for improvements to many current automated systems.

BRIEF SUMMARY

A method for operating a dynamic exertion system may involve receiving a rate of perceived exertion (RPE) through a user interface of a display device. The method may then combine the RPE with a movement, a movement load, and movement repetitions into movement set data. The method may then operate a dynamic exertion algorithm. The method may then display an adjusted movement information display comprising the prescribed load and the prescribed movement repetitions through the user interface, in response to configuration of a user interface controller with the display control.

The dynamic exertion algorithm may be configured to generate a prescribed load and prescribed movement repetitions from a one repetition maximum load value, historical movement set data, a relative exertion model and a calibration and adjustment model. The algorithm may then determine a difference in RPE from the expected RPE through operation of a comparator. The algorithm may then recalculate the one repetition maximum load value using the calibration and adjustment model when the difference in RPE is greater than an RPE threshold value. The algorithm may then generate a display control comprising the prescribed load and the prescribed movement repetitions.

In some configurations, the method may further involve operating the dynamic exertion algorithm to generate the prescribed movement repetitions from a maximum repetitions value, historical movement set data, a repetition-based relative exertion model and the calibration and adjustment model, wherein the repetition-based relative exertion model defines a relationship between the maximum repetitions value, movement repetitions, and the RPE, and the repetition-based relative exertion model determines an expected RPE. The algorithm may then determine the difference in RPE from the expected RPE through operation of the comparator. The algorithm may then recalculate the maximum repetitions value using the calibration and adjustment model when the difference in RPE is greater than an RPE threshold value. The algorithm may then generate the display control comprising the prescribed movement repetitions. The method may then involve displaying the adjusted movement information display comprising the prescribed movement repetitions through the user interface, in response to configuration of the user interface controller with the display control.

An apparatus may include a processor and memory. The memory may store instructions that, when executed by the processor, configure the apparatus to perform certain actions. The instructions may configure the processor to receive a rate of perceived exertion (RPE) through a user interface of a display device. The instructions may then configure the processor to combine the RPE with a movement, a movement load, and movement repetitions into movement set data. The instructions may then configure the processor to operate a dynamic exertion algorithm. The instructions may then configure the processor to display an adjusted movement information display comprising the prescribed load and the prescribed movement repetitions through the user interface, in response to configuration of a user interface controller with the display control.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
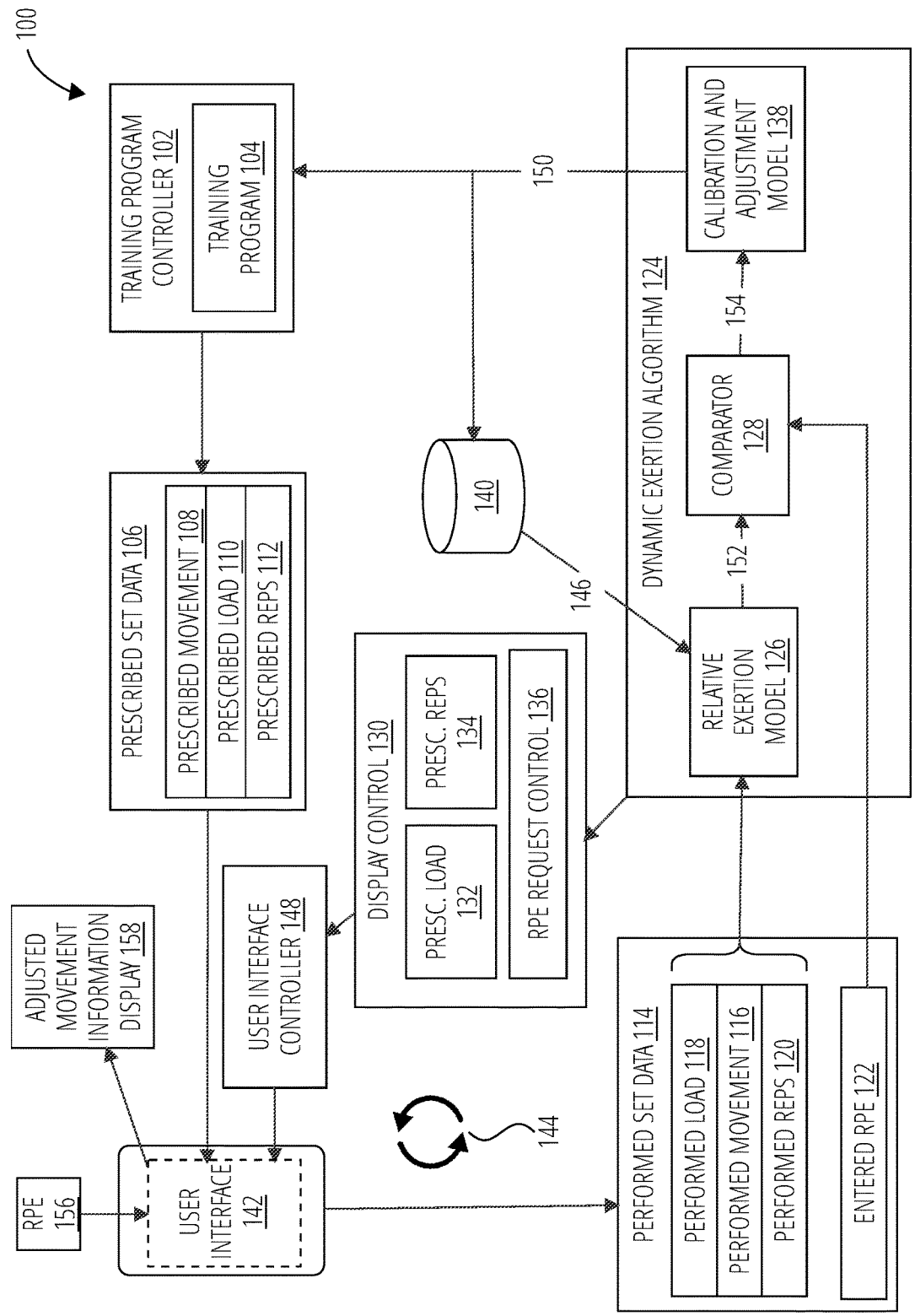
FIG. 1 illustrates a system 100 in accordance with one embodiment.

A method for the expert system to develop fitness training plans involves receiving a rate of perceived exertion (RPE) through a user interface of a display device. The system combines the RPE with a movement, a movement load, and movement repetitions into movement set data. The system then determines a difference in movement repetitions and a difference in RPE from the movement set data, historical movement set data, and an expected RPE through operation of a comparator. The system then operates a dynamic exertion algorithm. The dynamic exertion algorithm generates a prescribed load and prescribed movement repetitions from a one repetition maximum load value, historical movement set data, a relative exertion model and a calibration and adjustment model. The dynamic exertion algorithm may then determine a difference in RPE from the expected RPE through operation of a comparator. The dynamic exertion algorithm may then recalculate the one repetition maximum load value using the calibration and adjustment model when the difference in RPE is greater than an RPE threshold value. The dynamic exertion algorithm may then generate a display control comprising the prescribed load and the prescribed movement repetitions. The system then displays an adjusted movement information display comprising the prescribed load and the prescribed movement repetitions through the user interface, in response to configuration of a user interface controller with the display control.

In some embodiments, the adjusted movement information display comprises an RPE request in response to the user interface controller receiving an RPE request control with the display control.

In some embodiments, the RPE request control may be generated by the dynamic exertion algorithm from the historical movement set data.

In some embodiments, the dynamic exertion algorithm generates the prescribed load and the prescribed movement repetitions from related historical movement set data.

The method for a system to develop fitness training plans was developed primarily to solve two problems: (1) training load not being prescribed for all movements, and (2) the loading that was being prescribed may not be optimal for the exerciser at that time. A typical system would generally prescribe the loading for a given movement based on how much the exerciser could lift in a limited number of representative movements, such as: barbell bench press, barbell back squat and barbell hang clean. This meant that those three movements were essential for accurate loading prescription. If data for one or more were missing or out-of-date, then the loading for workouts would be missing or non-optimal.

The method for an expert system to develop fitness training plans solves these problems by decoupling the loading of every movement from a limited number of representative movements. In the method for the expert system to develop fitness training plans, each movement's loading may be calculated independently of any other movement's loading. The loading may also be updated on a set-by-set basis, instead of waiting for checkpoints in the training, sometimes months apart.

After a completed set, the system asks the exerciser for feedback on how difficult the set was, in the form of a 10 point RPE scale. Based on the difference between the exerciser inputted RPE, and the expected RPE of that set for that user (based on past performance on that movement) then the system will adjust the loading on that movement going forward.

The system may calculate loading for a given set with movement 1RMs such that the loading for a given movement may be independent from other lifts (such as bench press, squat, hang clean). The system accomplishes this since loading for every set may be calculated using the movement 1RM and target intensity for a given set using the following formula:

movement 1RM*target intensity %

The system may allow for user calibration such that prescribed loading for a movement is based on the first set a user performs. With some guidance, the user chooses an appropriate weight for the first set and enters RPE feedback. Calculations for the user calibration may be done by calculating the 1RM of the set that was completed (e.g., using the Epley formula), then dividing it by the Calibration Percentage associated with the entered RPE. In some configurations, the 1RM may be calculated utilizing a different formula instead of the Epley formula such as the Brzycki, McGlothin, Lombardi, Mayhew et al., O'Conner et al., Wathen, etc.

The method may utilize a version of the Epley formula to determine a 1RM.

$$1\ RM = w\left(1 + \frac{r}{30}\right)$$ Epley Formula

In the Epley formula, r is the number of repetitions performed and w is the amount of weight used (note that w is a factor of each formula, so the unit of measurement may not matter). The Epley formula assumes that r>1. The version may differ from it by the calibration percentage.

The system may also allow for related movement calibration from one or more related movements. Related movement calibration allows loading prescribed for a movement based on loading for related movements. Related movement calibration may be done in situation where a sport performance team designates one to three related movements for each movement that has dynamic loading enabled. If a movement 1RM exists for a related movement, then the first time a given movement is performed, an initial movement 1RM may be calculated. The related movement calibration may be calculated using the following formula:

(movement 1RM)=(related movement 1RM)*(correlation factor)

The system may save history of movement 1RMs allowing historical data of what the user is able lift for each movement to be accessible to the user in order to track their progress over time. The storing of every change to the movement 1RM for each movement for each exerciser may provide the system with a large data set to run analytics to help improve the system.

The system may be configured to only request RPE feedback at specific times. The system may be configured in this manner in order to avoid interruptions to the user while they are working out. The system may be configured to request RPE feedback at the first time a movement is ever performed and the last set of the day for each movement.

The system may be configured to make an adjustment to the movement 1RM on the last set performed (in the same workout) for at least one of the following conditions:

The system does not expect the user to be able to perform the set that they did in fact perform (system expected RPE>10)

The system expects the set performed to be too easy for the user (system expected RPE<1)

The set performed was different enough from the set prescribed (Absolute Value of (expected RPE−actual RPE)>1)

A movement has not been performed for an extended period of time (e.g., 8 weeks)

A workout has not been performed for an extended period of time (e.g., 2 weeks)

The system may adjust the movement 1RMs allowing adjustments to the movement load on future sets based on feedback. This adjustment may allow for the training to adjust to the user's strength levels. The system may adjust movement 1RM based on at least one or more of the following conditions:

Differences between expected RPE and the entered RPE (RPE Difference)

The completed intensity %=Entered Load/movement 1RM

The system finds the expected RPE at the intersection of the Completed Intensity % and Entered Reps on the relative intensity chart The RPE Difference=entered RPE−expected RPE, or If RPE difference is >=2 and <=4, then the system runs a movement 1RM adjustment algorithm to recalculate the movement 1RM.

The conditions for the adjustment may be part of the relative intensity adjustment algorithm.

The system may allow for re-calibration of the movement 1RM when a performed set is far off from expected in one or more of the following scenarios:

The set was harder or easier than expected (RPE Difference is >=4)

The performed set was a max effort set (Entered RPE is 10)

The performed set was harder than expected (expected RPE>10)

The performed set was (expected RPE<1) easier than expected.

The system may limit movement repetitions to a relatively high number, for example fifteen. The system may be configured to assume that if user performs more than fifteen reps, that the user wants sets that have at least fifteen reps. Note that "reps" may be used interchangeably with "repetitions" throughout this disclosure.

The system may specify which movements have dynamic loading enabled. Those that do not may use other methods for prescribing loading.

The system may allow for disabling and enabling of dynamic loading for a specific user in case the user wishes to return to the old system of prescribing loading.

In some configurations, a single repetition maximum (1RM) may be how much a user is able to lift in a single repetition. In some configurations, the rate of perceived exertion (RPE) is an estimate of how much effort a given action/movement took to complete and may be a value selected from a 10 point scale.

In some embodiments, a one repetition maximum load value (movement 1RM) is estimated for each movement and may be the number that the prescribed load is based on. A set 1RM is the 1RM of the entered load, entered reps, and entered RPE in accordance with values generated using the Epley formula and RPE load percentage.

The prescribed RPE is the RPE of the set that was prescribed. The system may calculate an expected RPE for a performed set for the user based off of their movement 1RM. The entered RPE is the RPE value that a user entered as a response to the RPE request. The RPE difference is the difference between the entered RPE and expected RPE (entered RPE−expected RPE). A relative intensity chart is a chart of data used for associating a given load percentage and the number of reps to an RPE score.

In some embodiments, the prescribed load is the weight that is prescribed by dynamic exertion algorithm for a given movement set. The prescribed repetitions is the number of repetitions that are prescribed by the dynamic exertion algorithm. The prescribed load may be adjusted in accordance with a prescribed intensity.

The prescribed intensity percentage is the intensity percentage that a set is given based on the movement, and where within the overall training plan the particular set appears. The entered loads and reps are the load and repetitions that the user enters through the user interface as part of the movement set inputs.

In some embodiments, the system utilizes a completed intensity percentage. The completed intensity percentage is a percentage value that may factor into the generation of the expected RPE. The completed intensity percentage is the intensity percentage of the entered load. The completed intensity percentage may be derived from the entered load divided by the movement 1RM.

In some embodiments, the system may undergo user calibration for estimating a movement 1RM and may be accomplished utilizing a plurality of different methods. A related movement calibration may be utilized for estimating a movement 1RM based on the user's strength levels on a related movement. The user calibration is the estimation of a movement 1RM based on the user's entered load, entered reps and entered RPE. The user calibration is derived by dividing the set 1RM by the starting percentage correlated to the entered RPE. A correlation factor may also be utilized, the correlation factor, is a percentage that is associated to a given entered RPE and is used in estimating a movement 1RM. A movement 1RM adjustment is a small adjustment (up or down) to a movement 1RM based on an adjustment percentage. The adjustment percentage is the amount of adjustment to a movement 1RM calculated by finding the percentage associated with RPE difference.

FIG. 1 illustrates a system 100 in accordance with one embodiment. The system 100 describes a configuration of the dynamic exertion system comprising a training program controller 102, a user interface 142, and a dynamic exertion algorithm 124 comprising a relative exertion model 126, a comparator 128, and calibration and adjustment model 138. The system 100 differs from the system 400, system 600, and system 700 as the one repetition maximum load value is included in an estimated maximum (eMax) value that considers the maximum load and the maximum number of repetitions (maximum repetitions value) for a particular movement.

In the system 100, a user interface 142 receives from the user performed set data 114, analogous to the movement set data, comprising performed load 118, performed movement 116, performed movement repetitions 120, and an entered RPE 122. The performed set data 114 is communicated to the dynamic exertion algorithm 124 comprising a relative exertion model 126, a comparator 128, and a calibration and adjustment model 138. The relative exertion model 126 receives the performed load 118, the performed movement 116, and the performed movement repetitions 120 as well as a historical eMax 146 from a controlled memory data structure 140 to determine an expected RPE 152. The relative exertion model 126 determination of the expected RPE 152 is similar to the use of the relative intensity chart but may look at the performed load 118 and the performed movement repetitions 120 for a performed movement 116. The entered RPE 122 is then communicated to the comparator 128 where it is compared to the expected RPE 152 to generate a difference in RPE 154. The 844 is then communicated to the calibration and adjustment model 138 in order to generate an adjusted eMax 150. The adjusted eMax 150 may then be communicated to the controlled memory data structure 140 to be utilized as historical eMax 146. The adjusted eMax 150 may then be communicated to the training program controller 102 comprising a training program 104. The training program 104 may utilize the adjusted eMax 150 to generate a prescribed set data 106 comprising a prescribed movement 108, a prescribed load 110, and prescribed movement repetitions 112. The prescribed set data 106 is communicated to the user interface 142 to be displayed to the user.

The one repetition maximum load value (1RM) is the estimated maximum load that a user may be able to perform on their next set. In an embodiment the 1RM may be substituted for an Estimated Max (eMax) that may refer to the 1RM and/or the estimated maximum reps that a user is able to perform. This is also to broaden it beyond loading to include reps-based data. eMax could still be an e1RM, which is a load that a person can lift once, but it also includes data such as Estimated Maximum repetitions, which is a maximum number of repetitions given a load (the load could be 0, like in the case of max number of push-ups). The eMax may serve as a measure of a user's ability level on a given movement.

The dynamic exertion algorithm 124 may generate a display control 130 comprising a prescribed load 132, prescribed repetitions 134, and an RPE request control 136. The RPE request control 136 may generate a prompt on the user interface 142 requesting an RPE 156 from the user. The system then displays an adjusted movement information display 158 comprising the prescribed load 132 and the prescribed repetitions 134 through the user interface 142, in response to configuration of a user interface controller 148 with the display control 130.

An example scenario describing the relative exertion model has been provided. In this scenario, a user has completed a movement set where the movement is a barbell bench press, the movement load is 120 lbs, and three repetitions were completed. The user's historical estimated maximum value for this particular movement set may differ as their previous maximum load was 171 lbs for this same movement and same number of repetitions.

In this scenario the user performed 70% of their Historical eMax (1 Rep Max) for the three repetitions. Based on this information, the relative exertion model may be utilized to estimate a rate of perceived exertion (RPE) as being a 6/10 from an RPE scale. The table 1 below is a simplified version of the Relative Exertion Model, with the Load % down the left side, reps across the top, and Estimated RPE in the body of the model.

TABLE 1

| Load % | Repetitions | | | | |
|---|---|---|---|---|---|
| | 1 | 2 | 3 | 4 | 5 |
| 100% | 10 | >10 | >10 | >10 | >10 |
| 90% | 8 | 9 | 10 | >10 | >10 |
| 80% | 6 | 7 | 8 | 9 | 9 |
| 70% | 4 | 5 | 6 | 6 | 7 |

This data may be populated using, for example, a combination of the Epley formula and experimentally determined values. These values may then be refined these numbers based on a regression analysis of thousands of performed sets. Another embodiment is to use machine learning to automatically refine the numerical values of the Relative exertion model 126 for different types of movements, or different users, even to a point of having different values for each user for each movement.

In another scenario, a user may be performing body weight exercises such as body weight push ups. In a set, the user was able to only perform five repetitions compared to their historical eMax of ten total repetitions with the same load (0 lbs) for the particular movement (Push-ups).

In this scenario, an embodiment of the Relative exertion model 126 may be utilized to estimate the RPE for the user's movement set. Based on the number of repetitions and their historical eMax, the user's RPE may be determined to be 7/10. The table 2 below is a simplified version of a repetition-based Relative Exertion Model, with the Historical eMax (max reps) down the left side, reps performed across the top, and Estimated RPE in the body of the model.

TABLE 2

| Historical eMax | Repetitions Performed | | | | |
|---|---|---|---|---|---|
| | 1 | 2 | 3 | 4 | 5 |
| 1 | 10 | >10 | >10 | >10 | >10 |
| 2 | 9 | 10 | >10 | >10 | >10 |
| 3 | 9 | 9 | 10 | >10 | >10 |
| 4 | 8 | 9 | 9 | 10 | >10 |
| 5 | 8 | 8 | 9 | 9 | 10 |
| 6 | 7 | 8 | 8 | 9 | 9 |
| 7 | 7 | 7 | 8 | 8 | 9 |
| 8 | 6 | 7 | 7 | 8 | 8 |
| 9 | 6 | 6 | 7 | 7 | 8 |
| 10 | 6 | 6 | 6 | 7 | 7 |

The purpose of the calibration and adjustment model 138 may be to determine what adjustments to make to the eMax based on the difference in estimated RPE and inputted RPE. In an embodiment, the calibration and adjustment model 138 may make determination according to the following scenarios:

If there is no difference in Estimated RPE and Inputted RPE, or if there is only a one point difference, the calibration and adjustment model may determine that there are no adjustments needed for the eMax.

If there is a two or three point difference, the calibration and adjustment model may call for 5-10% adjustments up or down to the eMax, according to the increase or decrease in the user's performance compared to their Historical eMax value.

If there is an RPE difference of 4+ points, the historical eMax value is determined to reflective of the user's current strength level and that their eMax value may need to be "re-calibrated" or re-calculated. In this example, the eMax value may be recalculated utilizing the Epley Formula.

Table 3 illustrates an example of the calibration and adjustment model.

TABLE 3

| RPE Difference | Adjustment to eMax | Note |
|---|---|---|
| 4 | Re-calibrate | Difference is Large Enough to Warrant Full Re-Calibration of the eMax |
| 3 | −10% | Large Adjustment - Reduce eMax by 10% |
| 2 | −5% | Small Adjustment - Reduce eMax by 5% |
| 1 | 0% | No Change - Difference is Small Enough to Not Warrant a Change |
| 0 | 0% | No Change |
| −1 | 0% | No Change - Difference is Small Enough to Not Warrant a Change |
| −2 | 5% | Small Adjustment - Increase eMax by 5% |
| −3 | 10% | Large Adjustment - Increase eMax by 10% |
| −4 | Re-calibrate | Difference is Large Enough to Warrant Full Re-Calibration of the eMax |

The training program controller 102 is an important piece to the feedback loop (feedback loop 144). The training program controller 102 comprises a training program 104 that is a pre-configured workout plan that the user is executing. The training program 104 comprises a series of sets in a given order, with the movement, the planned Load %, and planned Reps for each set. Utilizing the user's eMax, the training program controller generates the Prescribed Load and Prescribed Repetitions for the user. The Prescribed Load may be calculated by multiplying the Load % for the set that is determined in the Training Program with the eMax. Example calculations for loaded movement are found below:

Prescribed Movement: BB Bench Press (pre-determined by the Training Program)
Prescribed Load=Load % (pre-determined by the Training Program)*eMax
Prescribed Reps: 5 (pre-determined by the Training Program)

Figure 2:
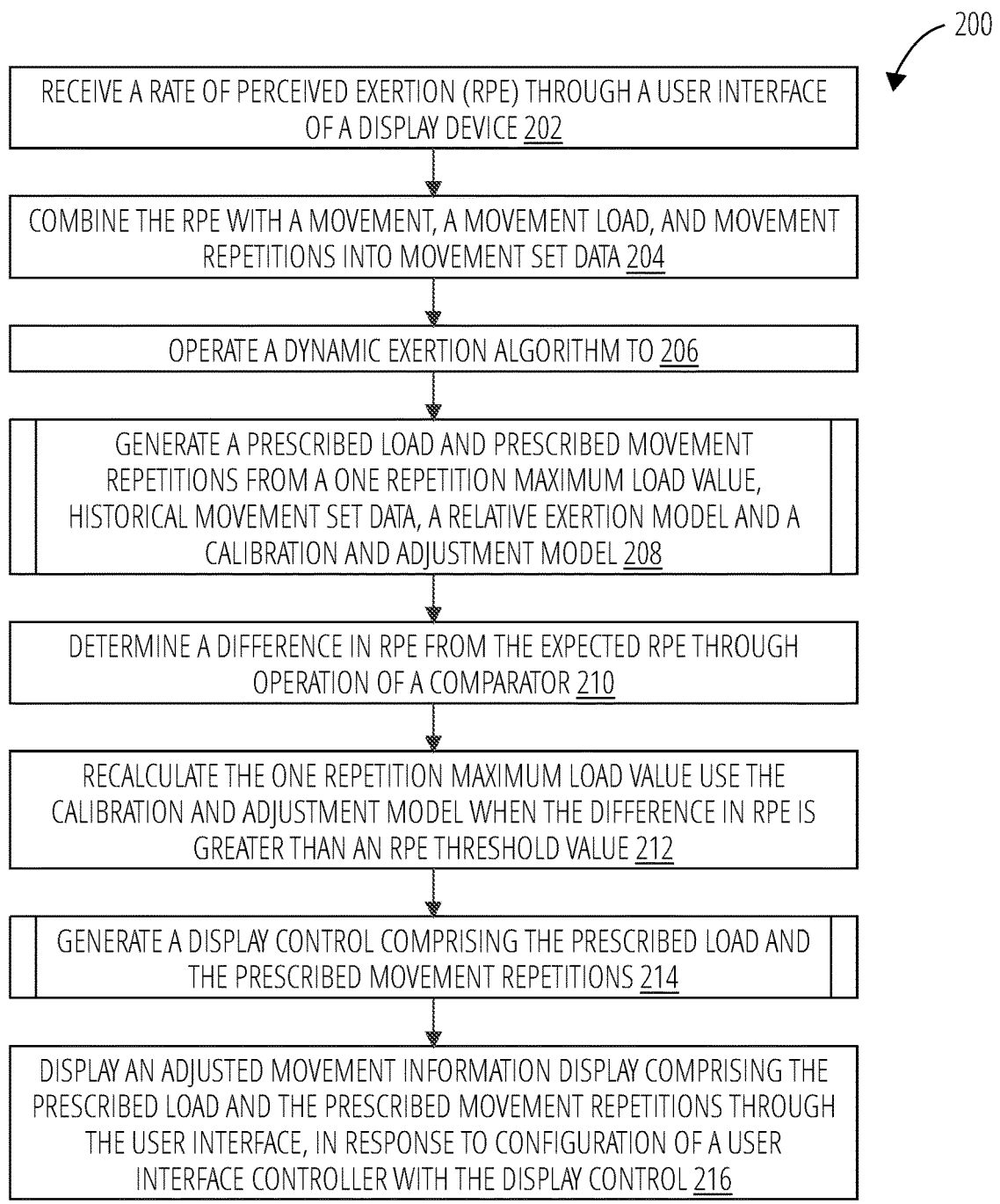
FIG. 2 illustrates a routine 200 in accordance with one embodiment.
Figure 3:
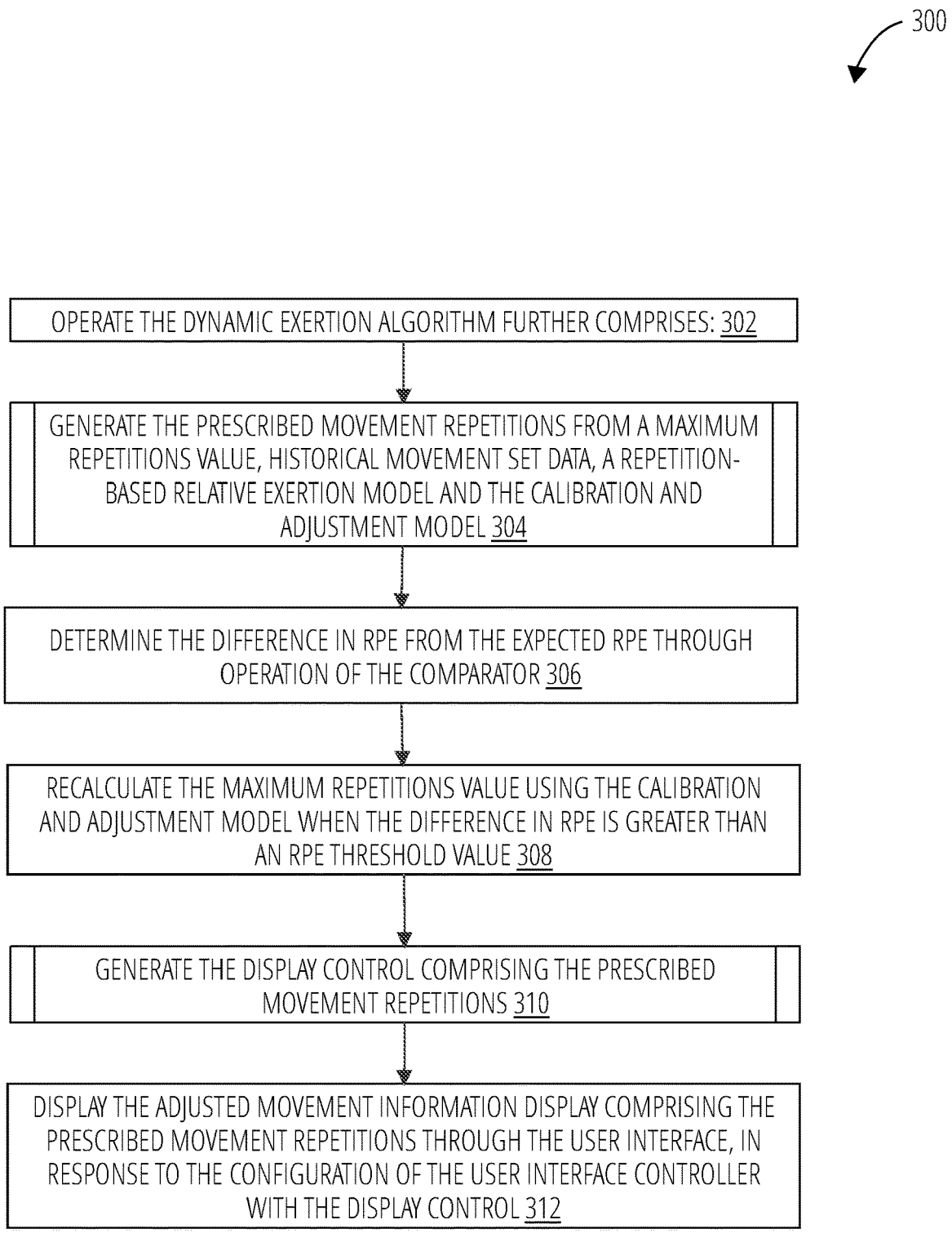
FIG. 3 illustrates a routine 300 in accordance with one embodiment.

The system 100 may be operated in accordance with the processes described in FIG. 2 and FIG. 3.

Referring to FIG. 2, in block 202, routine 200 receives a rate of perceived exertion (RPE) through a user interface of a display device. In block 204, routine 200 combines the RPE with a movement, a movement load, and movement repetitions into movement set data. In block 206, routine 200 operates a dynamic exertion algorithm to. In subroutine block 208, routine 200 generate a prescribed load and prescribed movement repetitions from a one repetition maximum load value, historical movement set data, a relative exertion model and a calibration and adjustment model, wherein the relative exertion model defines a relationship between the movement load, the movement repetitions, and the RPE, and the relative exertion model determines an expected RPE. In block 210, routine 200 determine a difference in RPE from the expected RPE through operation of a comparator. In block 212, routine 200 recalculate the one repetition maximum load value uses the calibration and adjustment model when the difference in RPE is greater than an RPE threshold value. In subroutine block 214, routine 200 generate a display control comprising the prescribed load and the prescribed movement repetitions. In block 216, routine 200 displays an adjusted movement information display comprising the prescribed load and the prescribed movement repetitions through the user interface, in response to configuration of a user interface controller with the display control.

Referring to FIG. 3, in block 302, routine 300 operates the dynamic exertion algorithm to further include: In subroutine block 304, routine 300 generates the prescribed movement repetitions from a maximum repetitions value, historical movement set data, a repetition-based relative exertion model and the calibration and adjustment model, wherein the repetition-based relative exertion model defines a relationship between the maximum repetitions value, movement repetitions, and the RPE, and the repetition-based relative exertion model determines an expected RPE. In block 306, routine 300 determines the difference in RPE from the expected RPE through operation of the comparator. In block 308, routine 300 recalculates the maximum repetitions value using the calibration and adjustment model when the difference in RPE is greater than an RPE threshold value. In subroutine block 310, routine 300 generates the display control comprising the prescribed movement repetitions. In block 312, routine 300 displays the adjusted movement information display comprising the prescribed movement repetitions through the user interface, in response to the configuration of the user interface controller with the display control.

Figure 4:
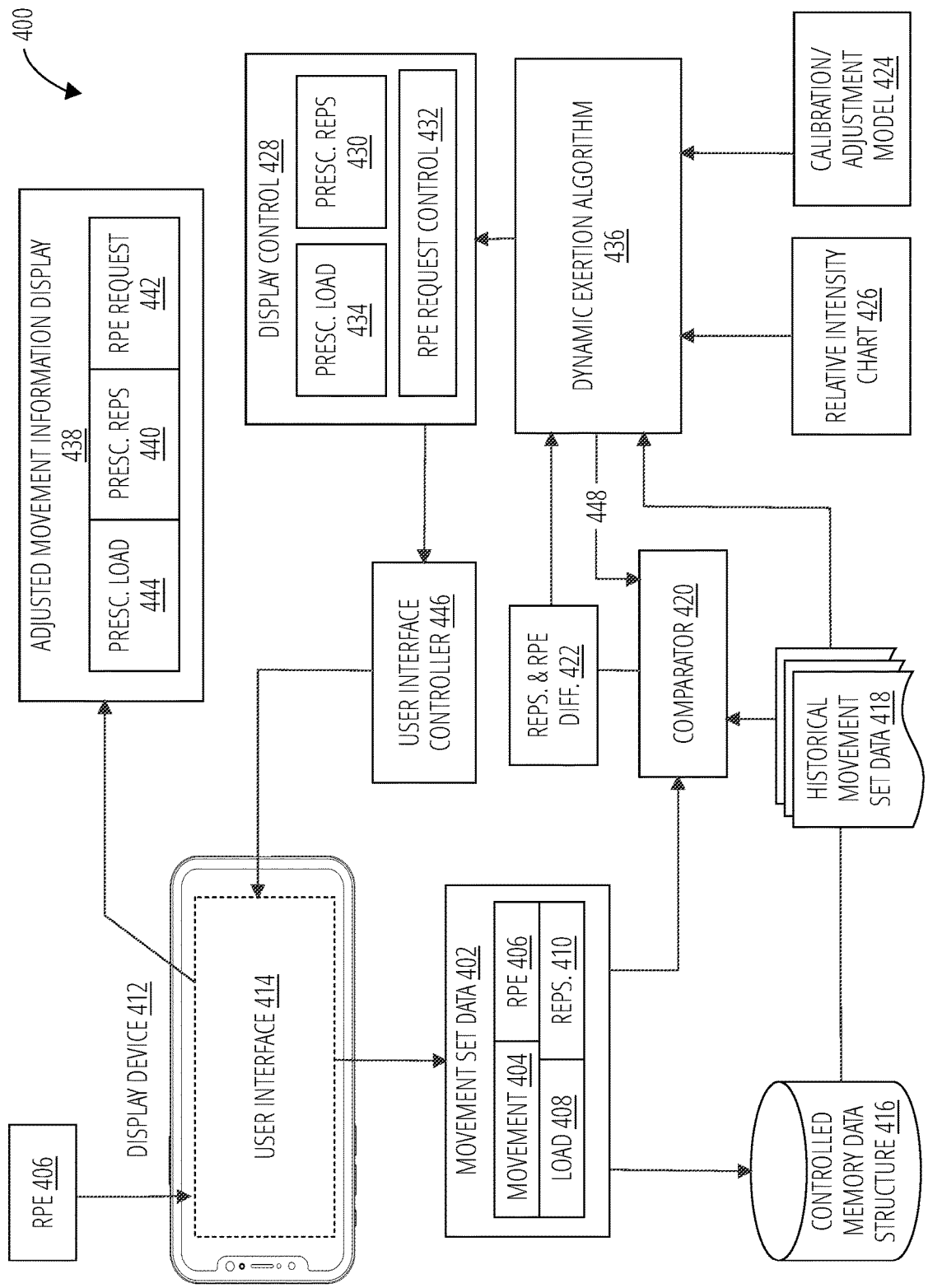
FIG. 4 illustrates a system 400 in accordance with one embodiment.

FIG. 4 illustrates a system 400 comprising a user interface 414, a controlled memory data structure 416, a comparator 420, a user interface controller 446, and a dynamic exertion algorithm 436. The user interface 414 is displayed on a display device 412 through operation of a user interface controller 446. The user interface 414 may receive a rate of perceived exertion (RPE 406). The RPE 406 may be combined with a movement 404, a movement load 408, and movement repetitions 410, in movement set data 402. The movement set data 402 may be communicated to a comparator 420 and a controlled memory data structure 416 where it may be aggregated as part of a historical movement set data 418. The comparator 420 may compare the current movement data set (movement set data 402) to the historical movement set data 418 and an expected RPE 448 from the dynamic exertion algorithm 436 to generate a difference in loading, movement repetitions and a difference in RPE (reps. & RPE diff. 422). The dynamic exertion algorithm 436 may utilize the loadings, reps. & RPE diff. 422 and a relative intensity chart 426 to generate a one repetition maximum load value (movement 1RM). The dynamic exertion algorithm 436 may utilize the movement 1RM, the calibration and adjustment model 424, the historical movement set data 418 to generate a prescribed load 434, prescribed repetitions 430, and an expected RPE 448. The dynamic exertion algorithm 436 generates a display control 428 at least comprising the prescribed load 434 and the prescribed repetitions 430. The display control 428 configures the user interface controller 446 to generate an adjusted movement information display 438 for display through the user interface 414. The adjusted movement information display 438 comprises a prescribed load 444 and prescribed repetitions 440. In some instances, an RPE request control 432 may be generated with the display control 428 to display an RPE request 442 with the adjusted movement information display 438. The RPE request control 432 may be generated by the dynamic exertion algorithm 436 based in part on the historical movement set data 418. The system 400 may be operated in accordance with the process described in FIG. 5.

Figure 5:
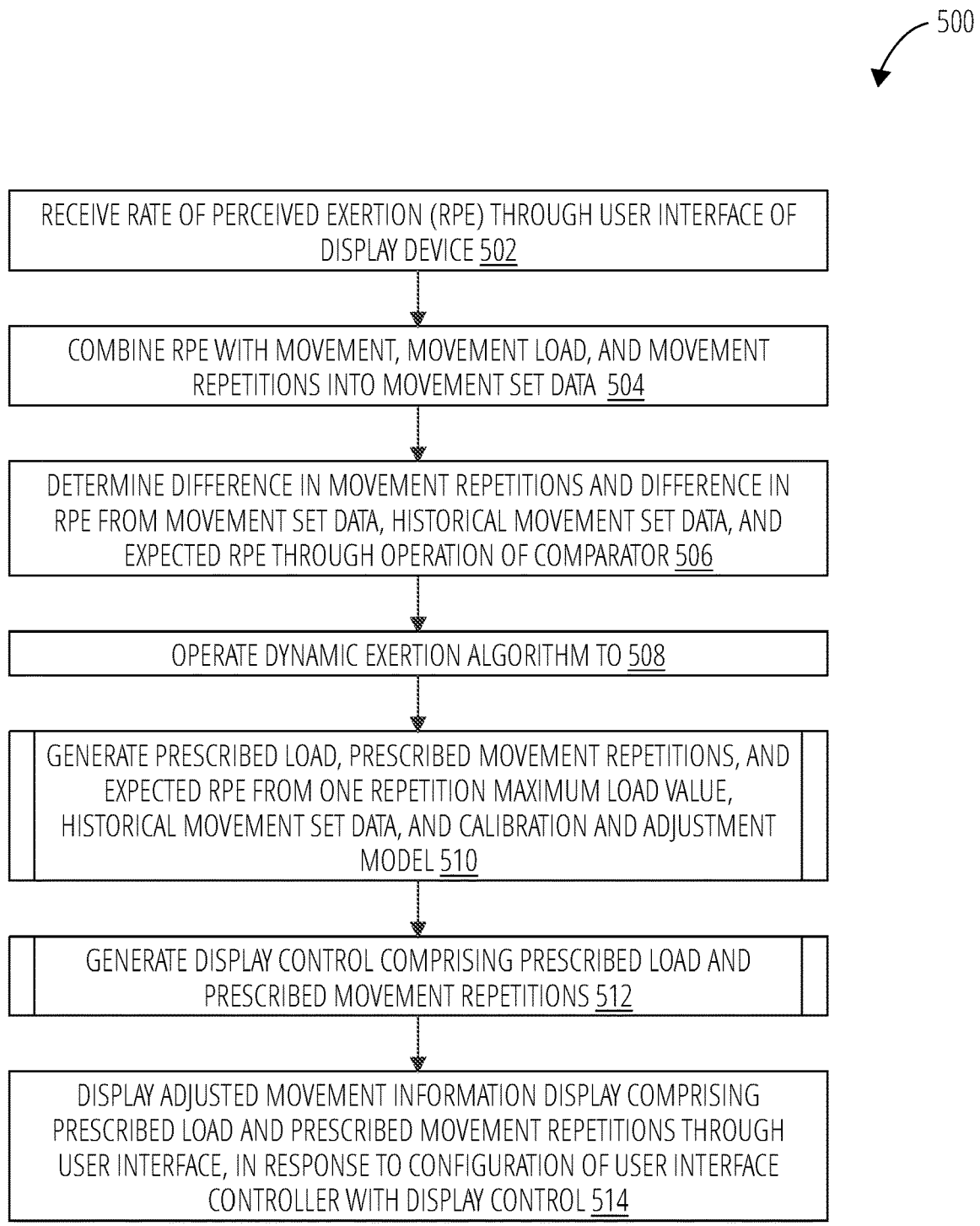
FIG. 5 illustrates a method 500 in accordance with one embodiment.

Referencing FIG. 5, a method 500 receives a rate of perceived exertion (RPE) through a user interface of a display device (block 502). In block 504, the method 500 combines the RPE with a movement, a movement load, and movement repetitions as movement set data. In block 506, the method 500 determines a difference in movement repetitions and a difference in RPE from the movement set data, historical movement set data, and an expected RPE through operation of a comparator. In block 508, the method 500 operates a dynamic exertion algorithm. In subroutine block 510, the dynamic exertion algorithm generates a prescribed load, prescribed movement repetitions, and an expected RPE from the one repetition maximum load value, the historical movement set data, and calibration and adjustment model. In subroutine block 512, the dynamic exertion algorithm generates a display control comprising the prescribed load and the prescribed movement repetitions. In block 514, the method 500 displays an adjusted movement information display comprising the prescribed load and the prescribed movement repetitions through the user interface, in response to configuration of a user interface controller with the display control.

Figure 6:
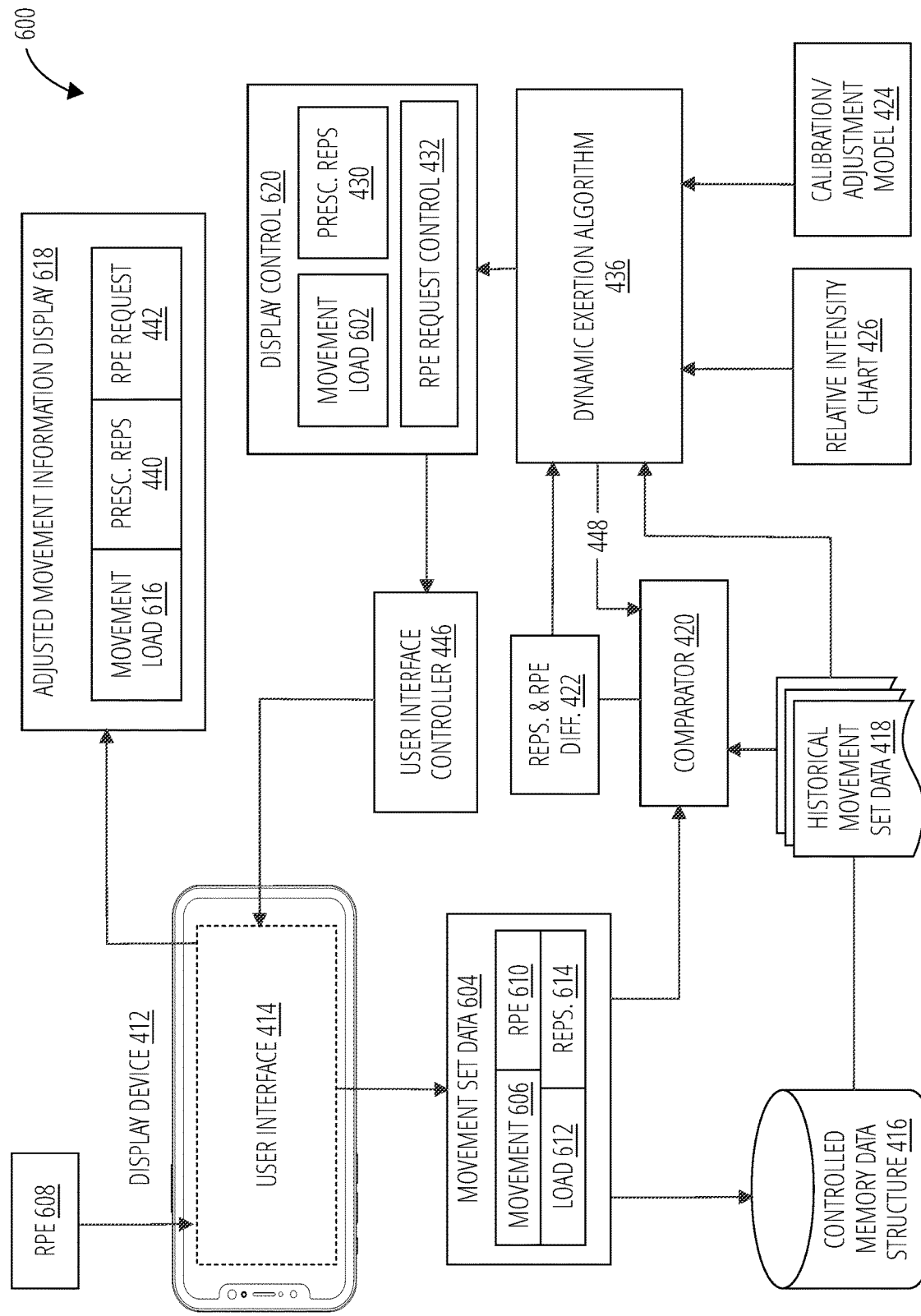
FIG. 6 illustrates a system 600 in accordance with one embodiment.

FIG. 6 illustrates a system 600 in accordance with one embodiment. The system 600 is similar to the system 400 in FIG. 4 but describes a scenario where the dynamic exertion algorithm 436 calculates that the movement load remains unchanged and generates a display control 620 comprising a movement load 602, prescribed repetitions 430, and an RPE request control 432. The display control 620 is utilized by the user interface controller 446 to display an adjusted movement information display 618 on the display device 412 comprising a movement load 616, the prescribed repetitions 440, and the RPE request 442.

The system 600 may be operated to receive a rate of perceived exertion (RPE 608) through a user interface 414 of a display device 412. The RPE 608 may then be combined with other configured exercise data, such as the movement 606, the movement load 612, and the movement repetitions 614, into movement set data 604. The movement set data 604 may then be compared to the previous values of the movement set data (historical movement set data 418) by way of a comparator 420. The movement set data 604 may aggregated into the historical movement set data 418 by being communicated to a controlled memory data structure 416. The comparator 420 determines a difference in movement repetitions and a difference in RPE (reps. & RPE diff. 422) from at least the movement set data 604, historical movement set data 418, and an expected RPE 448 generated from the dynamic exertion algorithm 436. The difference in RPE and the difference in reps may then be passed to the dynamic exertion algorithm 436. The dynamic exertion algorithm 436 may then be operated to generate a one repetition maximum load value from the difference in movement repetitions, the difference in RPE, and a relative intensity chart. The dynamic exertion algorithm 436 may then generate prescribed movement repetitions (prescribed repetitions 430) from the one repetition maximum load value, the historical movement set data (historical movement set data 418), and calibration and adjustment model 424. The calibration and adjustment model 424 may define a relationship between movement load 612, movement repetitions 614, and RPE 610. The dynamic exertion algorithm 436 may combine the determined values for the movement load 602 and the prescribed repetitions 430 to generate a display control 620 that includes an RPE request control 432 requesting an RPE from the user after the next movement set.

The display control 620 is communicated to a user interface controller 446 for controlling the user interface 414 of a display device 412. The user interface controller 446 is configured with the display control 620 to generate an adjusted movement information display 618 displayed in the user interface 414 showing a movement load 616 and a prescribed repetitions 440, as well as an RPE request 442 for the user's next movement set.

Figure 7:
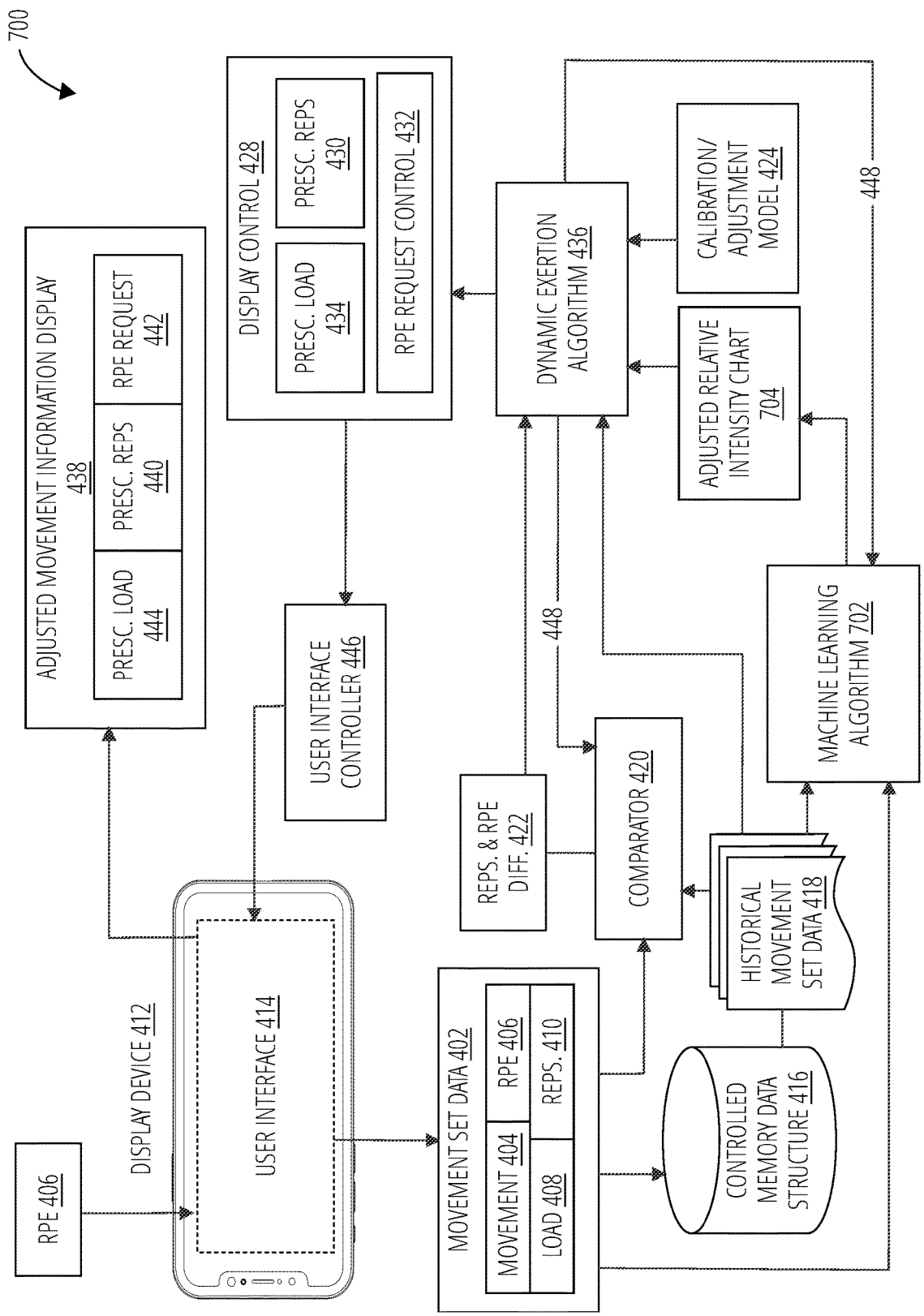
FIG. 7 illustrates a system 700 in accordance with one embodiment.

FIG. 7 illustrates a system 700 in accordance with one embodiment. The system 700 is similar to the system 400 of FIG. 4 and system 600 in FIG. 6 but includes a machine learning algorithm 702 that may be utilized to adjust the relative intensity chart to generate an adjusted relative intensity chart 704.

In the system 700, the display device 412 receives an RPE 406 value and other values of the movement set data 402 through the user interface 414. In some instances, the information for the movement set data 402 may already be entered if the user is in the middle of a set of exercises. The movement set includes the movement 404, the movement load 408, and the movement repetitions 410. The movement set data 402 would be communicated to the controlled memory data structure 416 for storage where it may be stored as part of the historical movement set data 418 as well as to the comparator 420. The comparator 420 determines a difference in repetitions from the current movement set data and the historical movement set data. The difference in movement repetitions is then communicated to the dynamic exertion algorithm 436 where the difference in repetitions and a previously calculated one repetition maximum load value are utilized to generate a new expected RPE (expected RPE 448) the new expected RPE 448 may then be communicated back to the comparator 420 to calculate the difference between the RPEs. The difference in Reps and RPEs (reps. & RPE diff. 422) are then utilized by the dynamic exertion algorithm 436 to determine a prescribed load 434 and prescribed repetitions 430 through the calibration and adjustment model 424 and the one repetition maximum load value. The prescribed load 434 and the prescribed repetitions 430 are then communicated with an RPE request control 432 as a display control 428 to the user interface controller 446 which configures the user interface 414 to display an adjusted movement information display 438 comprising the prescribed load 444, prescribed repetitions 440, and an RPE request 442.

Figure 11:
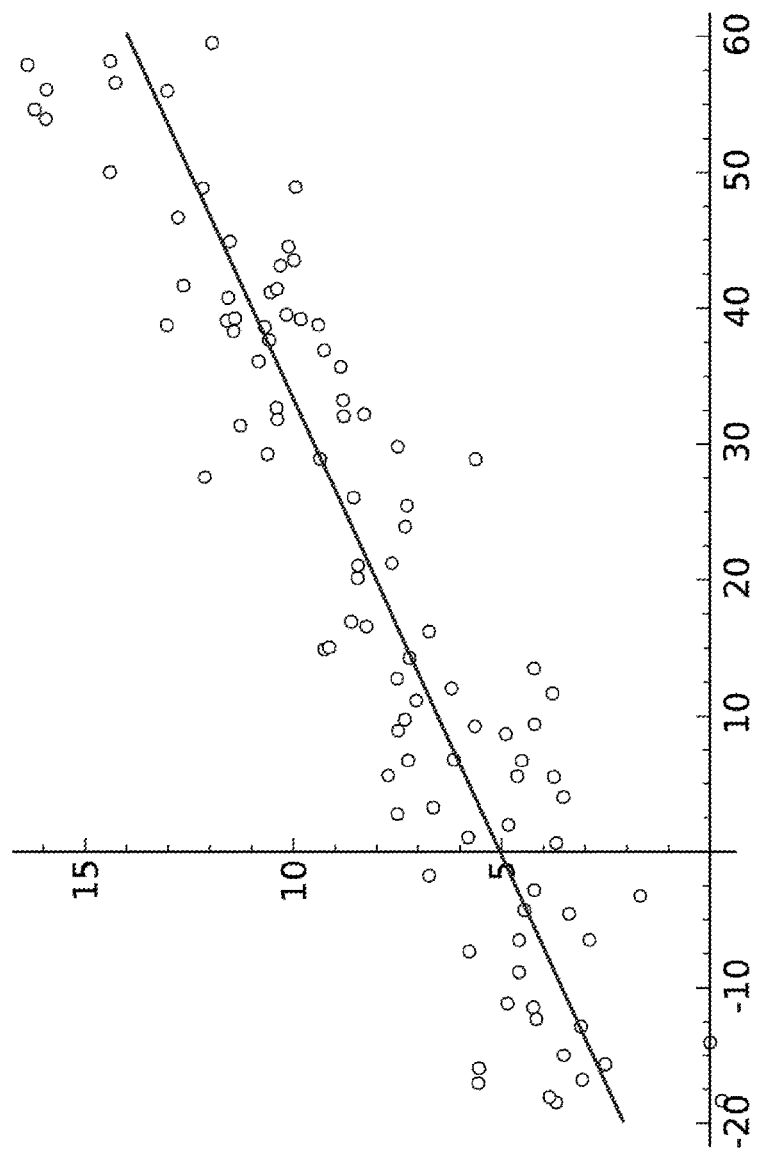
FIG. 11 illustrates a graph 1100 showing a best fit line.

In the system 700, a machine learning algorithm 702 may be positioned to receive the movement set data 402 and the historical movement set data 418 as well as the expected RPE 448 for a particular movement set. The machine learning algorithm 702 may perform regression analysis on the movement set data 402 and the historical movement set data 418 to determine signs of user fatigue which may be indicated in differences between the entered RPE and the expected RPE. This determination may be utilized to adjust the expected RPEs for with adjusted values for completed intensity percentage against the performed number of movement repetitions for a particular movement set generating an adjusted relative intensity chart 704. The regression analysis performed by the machine learning algorithm 702 may take into consideration the expected RPE 448 values along with the values for the prescribed load and prescribed movement repetitions for a current movement set. In some configurations, the machine learning algorithm 702 may perform the actions of relative intensity adjustment algorithm. Further details regarding the regression analysis may be found in FIG. 11 and FIG. 12.

Figure 8:
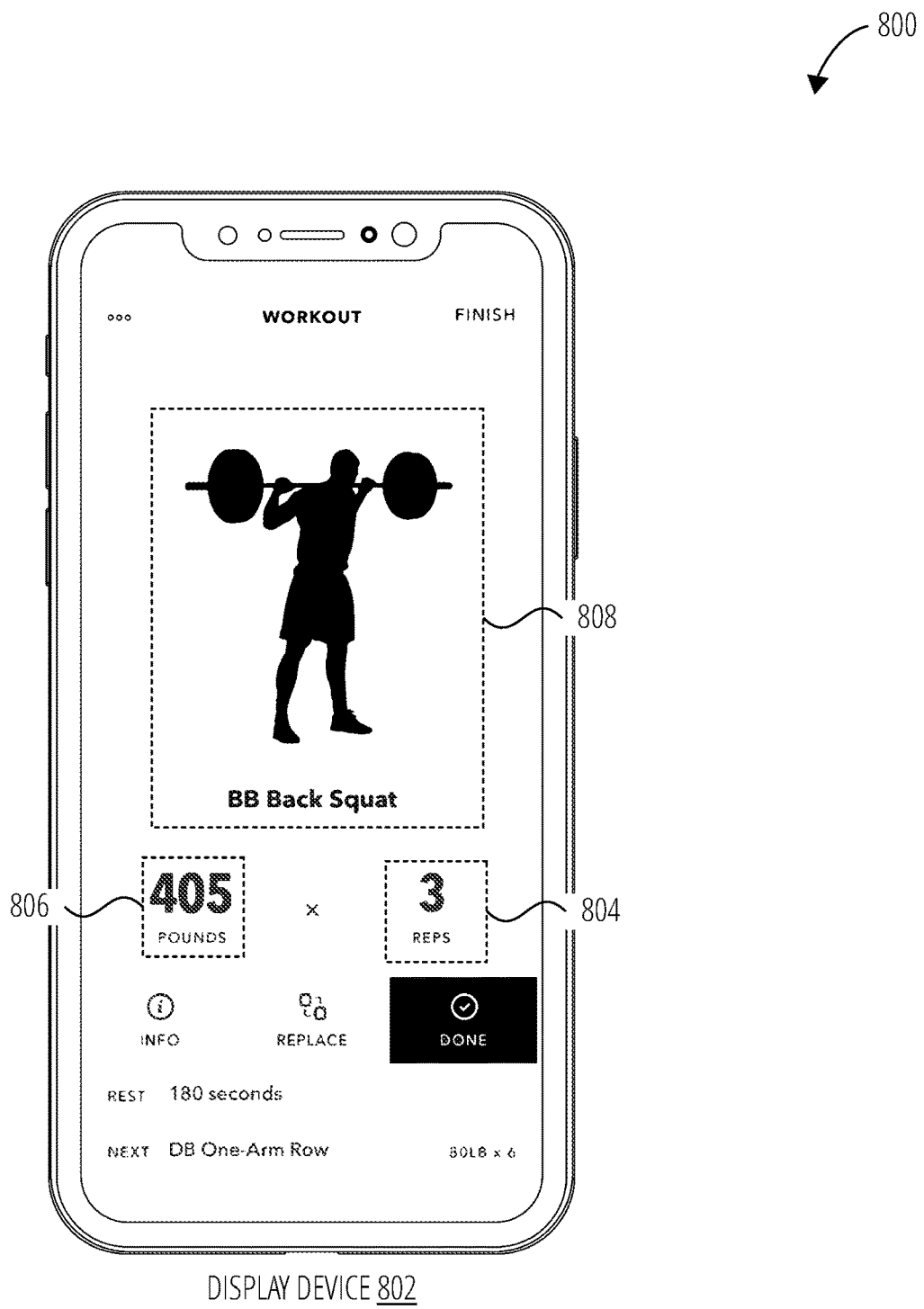
FIG. 8 illustrates a user interface 800 in accordance with one embodiment.

FIG. 8 illustrates a user interface 800 displayed on a display device 802. The user interface 800 comprises a movement 808, a movement load 806, and number of movement repetitions 804. The user may set the movement load 806 initially or the value may be populated by the system. The movement repetitions 804 may be the target number of repetitions or the number of repetitions entered by the user at the end of the set. The movement 808 may be displayed with a prescribed load for the movement load 806, and a number of prescribed movement repetitions following completion of a different movement set.

Figure 9:
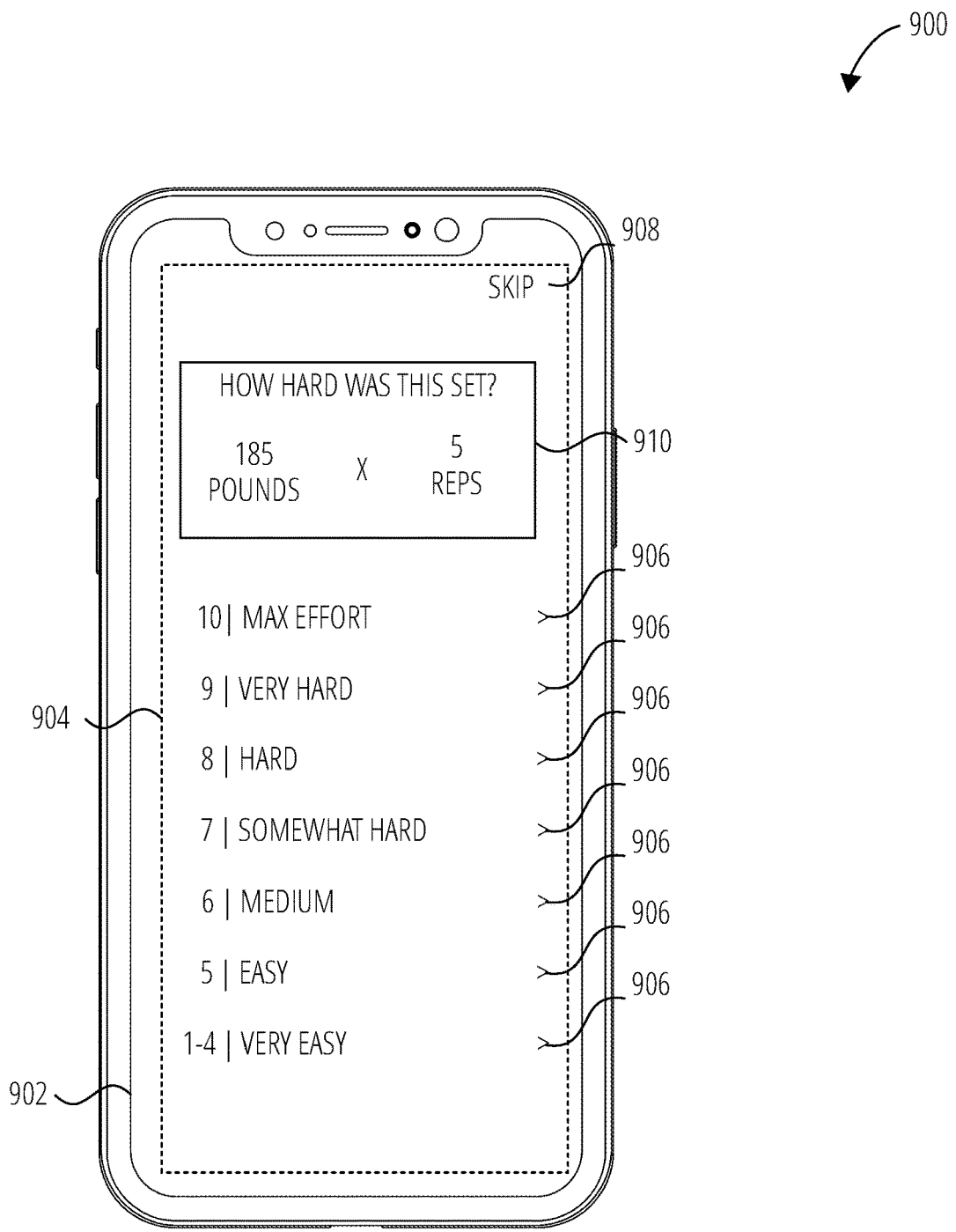
FIG. 9 illustrates a display device 900 in accordance with one embodiment.

FIG. 9 illustrates a display device 900 displaying a user interface 902 in accordance with one embodiment. The display device 900 shows an embodiment of an RPE request 904 displayed in the user interface 902 comprising previous set information 910, selectable RPE values (RPE scores 906), ranging between 1 and 10, and a skip button 908.

The previous set information 910 displays information related to the previous set performed by the user. In this example, the previous set information 910 includes the movement load and the number of movement repetitions performed by the user. The previous set information 910 may include questions asking the user how difficult the previous set was. While the question asking the user about the difficulty of the previous set is found in the previous set information 910, it may be found anywhere within the RPE request 904. In some configurations the question may appear before the RPE request 904 is displayed on the user interface 902.

The user may respond to the question in the previous set information 910 by selecting one of the RPE scores 906. The RPE scores 906 are listed ranging from 10 to 1 but shown as seven different option buttons that can be selected by the user. The first button from the top is rated as a ten and the lowest button is for ratings below five (1-4). Ten is "maximum effort", nine is "very hard", eight is "hard", seven is "somewhat hard", six is "medium", and five is "easy". Scores between 1-4 are grouped together in the same button as a score below five is considered "very easy". The organizations of the values are useful in the calculations of the adjusted movement load by including the lower limit threshold value. In some configurations, the displayed number of rating options may or may not include values and a description. Additionally, some variations may have a different number of options from which a user may select.

The skip button 908 is a button that may be provided to the user if they wish to skip submitting an RPE. This may occur if the user is done with their work out as well as other reasons. If the user skips submitting an RPE, the system may default to the previous set recommendations. In other scenarios, skipping the RPE may be viewed by the system that the user has finished working out.

Figure 10:
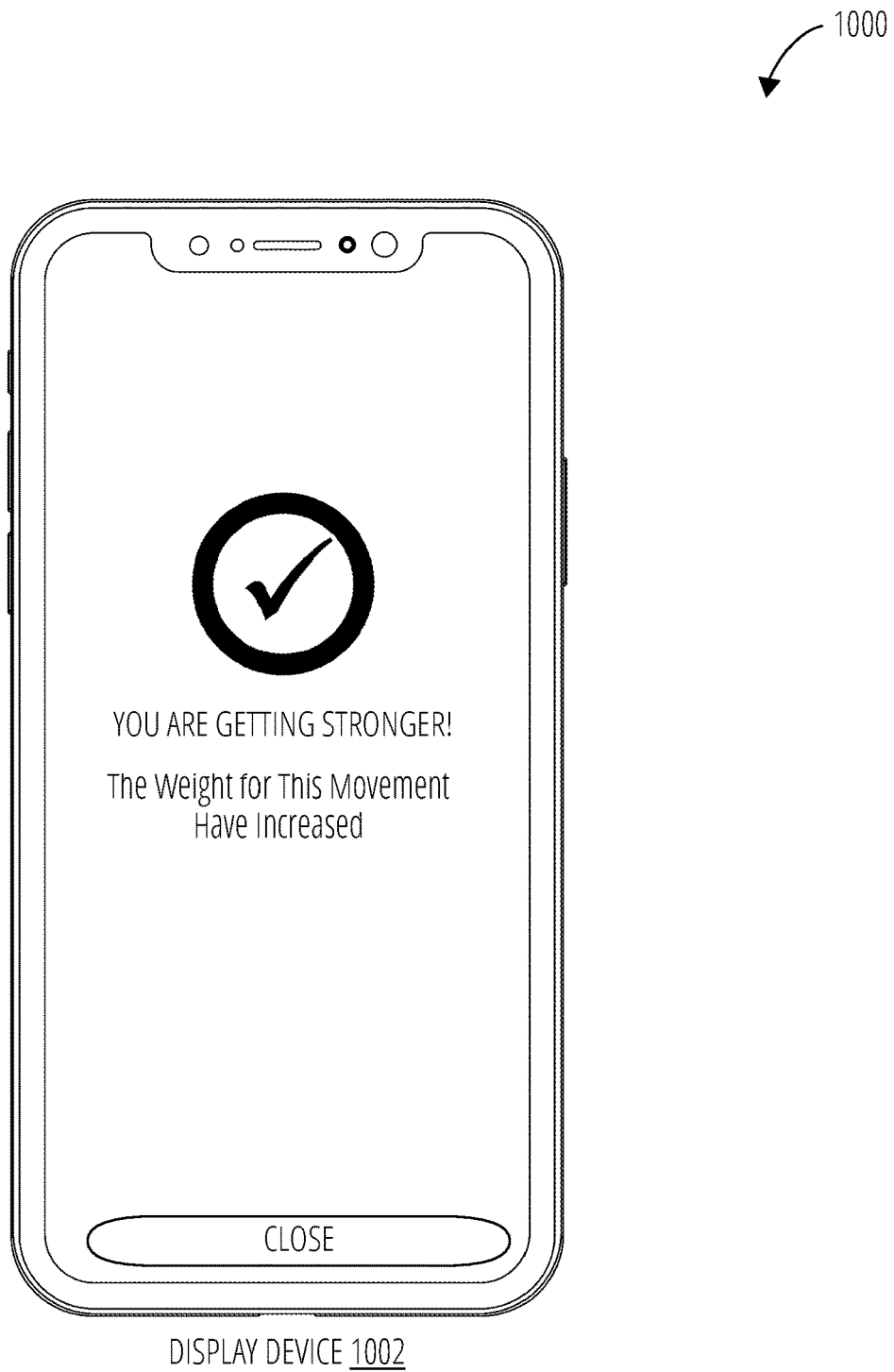
FIG. 10 illustrates a user interface 1000 in accordance with one embodiment.

FIG. 10 illustrates a user interface 1000 displayed on a display device 1002 showing a notification to the user that they system is adjusting the prescribed load according to their RPE for the previous set. In the user interface 1000 the user may receive a notification after entering their RPE for a set that informs them that prescribed load is set to increase in response to the RPE that the user entered. To motivate the user the notification may be worded such that it compliments the user for achieving a greater strength level. For instance, the display device 1002 in the user interface 1000 states that "you are getting stronger" followed by the message that the weight for the particular movement has increased. In some configurations, the user interface 1000 may display additional information, such as notifying the user the amount by which the weight increased, showing the new weight value for the exercise, and/or showing the user statistics related to their improvement overtime, etc. The user statistics may show the user their progress from weight training over a period of such as from the start of using the system.

Regression is a method of modelling a target value based on independent predictors. This method is mostly utilized for forecasting and determining cause and effect relationship between variables. Regression techniques mostly differ based on the number of independent variables and the type of relationship between the independent and dependent variables.

Simple linear regression is a type of regression analysis where the number of independent variables is one and there is a linear relationship between the independent(x) and dependent(y) variable. Referencing FIG. 11, the line in the graph 1100 is referred to as the best fit straight line. Based on the given data points, a line is plotted that models the points the best. The line may be modelled based on the linear equation $y=\alpha_0+\alpha_1*x$.

The motive of the linear regression algorithm is to find the best values for $\alpha_0$ and $\alpha_1$.

Regression analysis includes a set of machine learning methods that allows for the prediction of a continuous outcome variable (y) based on the value of one or multiple predictor variables (x).

The goal of a regression model is to build a mathematical equation that defines y as a function of the x variables. This equation may be utilized to predict the outcome (y) on the basis of new values of the predictor variables (x).

Linear regression is a technique for predicting a continuous variable. It assumes a linear relationship between the outcome and the predictor variables.

The linear regression equation may be written as $y=b0+b*x+e$, where:
   b0 is the intercept,
   b is the regression weight or coefficient associated with the predictor variable x.
   e is the residual error Technically, the linear regression coefficients are determined so that the error in predicting the outcome value is minimized. This method of computing the beta coefficients is called the Ordinary Least Squares method.

When there are multiple predictor variables, say x1 and x2, the regression equation may be written as $y=b0+b1*x1+b2*x2+e$. In some situations, there might be an interaction effect between some predictors, that is for example, increasing the value of a predictor variable x1 may increase the effectiveness of the predictor x2 in explaining the variation in the outcome variable. Note also that, linear regression models can incorporate both continuous and categorical predictor variables.

When building a linear regression model, diagnostics are performed to determine whether linear model is suitable for a data set. In some cases, the relationship between the outcome and the predictor variables may not be linear. In these situations, a non-linear regression, such as polynomial and spline regression, may be utilized.

When there are multiple predictors in the regression model, it may be necessary to select the best combination of predictor variables to build an optimal predictive model. This process is called model selection, and includes comparing multiple models containing different sets of predictors in order to select the best performing model that minimize the prediction error. Linear model selection approaches include best subsets regression and stepwise regression In some situations, such as in genomic fields, a data set may be a large multivariate data set containing some correlated predictors. In this case, the information, in the original data set, may be summarized into few new variables (called principal components) that are a linear combination of the original variables. This few principal components may be used to build a linear model, which might be more performant for the data. This approach is known as principal component-based methods, which includes principal component regression and partial least squares regression.

An alternative method to simplify a large multivariate model is to use penalized regression, which penalizes the model for having too many variables. The most well known penalized regression include ridge regression and the lasso regression.

Although all these different regression models can be applied to a data set, comparison of the models may be needed to select the best approach that best explains data-set. To do so, statistical metrics may be utilized to compare the performance of the different models in explaining the data set and in predicting the outcome of new test data.

The best model may be defined as the model that has the lowest prediction error. The most popular metrics for comparing regression models, include:
   Root Mean Squared Error, which measures the model prediction error. It corresponds to the average difference between the observed known values of the outcome and the predicted value by the model. RMSE is computed as RMSE=mean((observed−predicted)^2) %>% sqrt( ). The lower the RMSE, the better the model.

Adjusted R-square, representing the proportion of variation (i.e., information), in the data set, explained by the model. This corresponds to the overall quality of the model. The higher the adjusted R2, the better the model Note that, the above mentioned metrics should be computed on a new test data that has not been used to train (i.e., build) the model. If using a large data set with many records, the data can be split into training set (80% for building the predictive model) and test set or validation set (20% for evaluating the model performance).

One of the most robust and popular approach for estimating a model performance is k-fold cross-validation. It may be applied even on a small data set. k-fold cross-validation works as follow:
1. Randomly split the data set into k-subsets (or k-fold) (for example 5 subsets)
2. Reserve one subset and train the model on all other subsets
3. Test the model on the reserved subset and record the prediction error
4. Repeat this process until each of the k subsets has served as the test set.
5. Compute the average of the k recorded errors. This is called the cross-validation error serving as the performance metric for the model.

Taken together, the best model is the model that has the lowest cross-validation error, RMSE.

To better understand linear regression the concepts of a cost function and gradient descent are explained below.

The cost function is useful for determining the best possible values for $\alpha_0$ and $\alpha_1$ which would provide the best fit line for the data points. To determine the best values for $\alpha_0$ and $\alpha_1$, the search problem is converted into a minimization problem where the objective is to minimize the error between the predicted value and the actual value.

$$\text{minimize} \frac{1}{n}\sum_{i=1}^{n}(pred_i - y_i)^2 \quad \text{Function 1}$$

$$J = \frac{1}{n}\sum_{i=1}^{n}(pred_i - y_i)^2$$

The function above (function 1) was selected to illustrate the minimization problem. The difference between the predicted values and ground truth measures the error difference. The error difference is squared, then all data points summed up and the value is then divided by the total number of data points. This provides the average squared error over all the data points. Therefore, this cost function is also known as the Mean Squared Error(MSE) function. Utilizing this MSE function the values of $\alpha_0$ and $\alpha_1$ are changed such that the MSE value settles at the minima.

Gradient descent is a method of updating $\alpha_0$ and $\alpha_1$ to reduce the cost function(MSE). It is a process of optimizing the values of the coefficients by iteratively minimizing the error of the model on the training data. The idea is to start with some values for $\alpha_0$ and $\alpha_1$ and then change these values iteratively to reduce the cost. Gradient descent helps to determine how to change the values.

Gradient descent works by starting with random values for each coefficient. The sum of the squared errors is calculated for each pair of input and output values. A learning rate is used as a scale factor and the coefficients are updated in the direction towards minimizing the error. The process is repeated until a minimum sum squared error is achieved or no further improvement is possible.

In this method, a learning rate (alpha) parameter is selected that determines the size of the improvement step taken on each iteration of the procedure.

Figure 12:
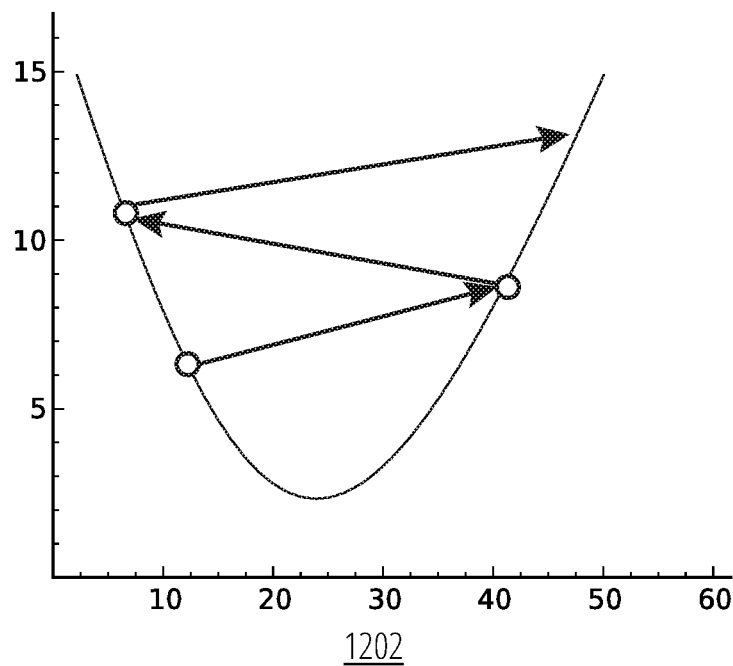
FIG. 12 displays a set graphs as examples of different learning rates.
Figure 12:
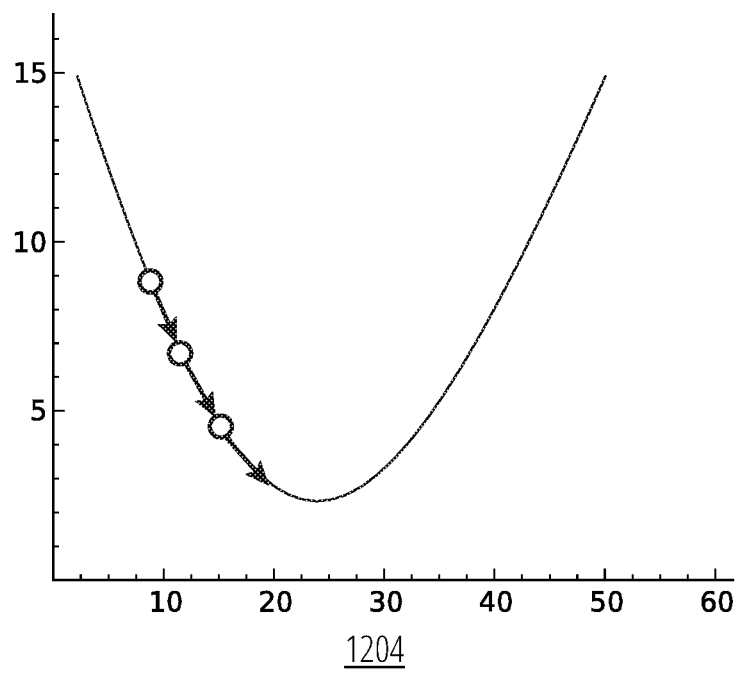

To draw an analogy, imagine a pit in the shape of U and you are standing at the topmost point in the pit and your objective is to reach the bottom of the pit. There is a catch, you can only take a discrete number of steps to reach the bottom. If you decide to take one step at a time you would eventually reach the bottom of the pit, but this would take a longer time. If you choose to take longer steps each time, you would reach sooner but, there is a chance that you could overshoot the bottom of the pit and not exactly at the bottom. In the gradient descent algorithm, the number of steps taken is the learning rate. This decides on how fast the algorithm converges to the minima. This concept is illustrated in FIG. 12 where graph 1202 illustrates a big learning rate the overshoots the minima, and graph 1204 illustrates a small learning rate as it approaches the minima.

In some situations, the cost function may be a non-convex function where there may be local minima but for linear regression, it is generally a convex function.

To update $\alpha_0$ and $\alpha_1$ utilizing gradient descent, gradients are taken from the cost function. To find these gradients, partial derivatives are taken with respect to $\alpha_0$ and $\alpha_1$. An example of how to identify the partial derivatives are found in the equations below $$J = \frac{1}{n}\sum_{i=1}^{n}(pred_i - y_i)^2$$

$$J = \frac{1}{n}\sum_{i=1}^{n}(a_0 + a_1 \cdot x_i - y_i)^2$$

$$\frac{\partial J}{\partial a_0} = \frac{2}{n}\sum_{i=1}^{n}(a_0 + a_1 \cdot x_i - y_i) \Rightarrow \frac{\partial J}{\partial a_0} = \frac{2}{n}\sum_{i=1}^{n}(pred_i - y_i)$$

$$\frac{\partial J}{\partial a_0} = \frac{2}{n}\sum_{i=1}^{n}(a_0 + a_1 \cdot x_i - y_i) \cdot x_i \Rightarrow \frac{\partial J}{\partial a_1} = \frac{2}{n}\sum_{i=1}^{n}(pred_i - y_i) \cdot x_i$$

$$a_0 = a_0 - \alpha \cdot \frac{2}{n}\sum_{i=1}^{n}(pred_i - y_i)$$

$$a_1 = a_1 - \alpha \cdot \frac{2}{n}\sum_{i=1}^{n}(pred_i - y_i) \cdot x_i$$

The partial derivates are the gradients and they are utilized to update the values of $\alpha_0$ and $\alpha_1$. Alpha is the learning rate which is a hyperparameter that requires a user to specify. Selecting a smaller learning rate may converge at the minima with more accurate results but at the cost of more time, while selecting a larger learning rate may converge sooner but there is a chance that to overshoot the minima.

Gradient descent is often taught using a linear regression model because it is relatively straightforward to understand. In practice, it is useful when implemented with a very large dataset either in the number of rows or the number of columns that may not fit into memory.

Figure 13:
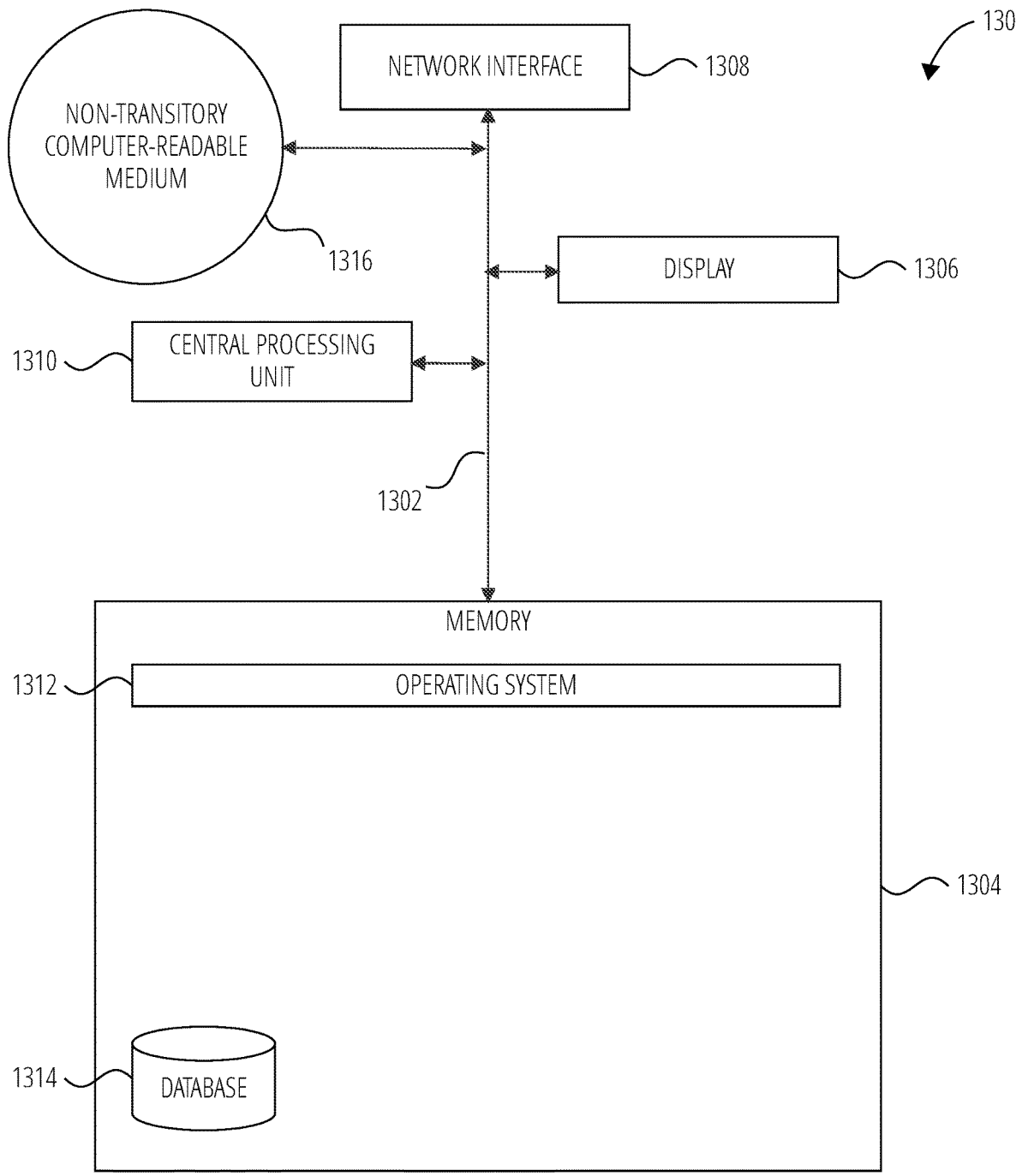
FIG. 13 illustrates a system 1300 in accordance with one embodiment.

FIG. 13 illustrates several components of an exemplary system 1300 in accordance with one embodiment. In various embodiments, system 1300 may include a desktop PC, server, workstation, mobile phone, laptop, tablet, set-top box, appliance, or other computing device that is capable of performing operations such as those described herein. In some embodiments, system 1300 may include many more components than those shown in FIG. 13. However, it is not necessary that all of these generally conventional components be shown in order to disclose an illustrative embodiment. Collectively, the various tangible components or a subset of the tangible components may be referred to herein as "logic" configured or adapted in a particular way, for example as logic configured or adapted with particular software or firmware.

In various embodiments, system 1300 may comprise one or more physical and/or logical devices that collectively provide the functionalities described herein. In some embodiments, system 1300 may comprise one or more replicated and/or distributed physical or logical devices.

In some embodiments, system 1300 may comprise one or more computing resources provisioned from a "cloud computing" provider, for example, Amazon Elastic Compute Cloud ("Amazon EC2"), provided by Amazon.com, Inc. of Seattle, Wash.; Sun Cloud Compute Utility, provided by Sun Microsystems, Inc. of Santa Clara, Calif.; Windows Azure, provided by Microsoft Corporation of Redmond, Wash., and the like.

System 1300 includes a bus 1302 interconnecting several components including a network interface 1308, a display 1306, a central processing unit 1310, and a memory 1304.

Memory 1304 generally comprises a random access memory ("RAM") and permanent non-transitory mass storage device, such as a hard disk drive or solid-state drive. Memory 1304 stores an operating system 1312.

These and other software components may be loaded into memory 1304 of system 1300 using a drive mechanism (not shown) associated with a non-transitory computer-readable medium 1316, such as a DVD/CD-ROM drive, memory card, network download, or the like.

Memory 1304 also includes database 1314. In some embodiments, system 1300 may communicate with database 1314 via network interface 1308, a storage area network ("SAN"), a high-speed serial bus, and/or via the other suitable communication technology.

In some embodiments, database 1314 may comprise one or more storage resources provisioned from a "cloud storage" provider, for example, Amazon Simple Storage Service ("Amazon S3"), provided by Amazon.com, Inc. of Seattle, Wash., Google Cloud Storage, provided by Google, Inc. of Mountain View, Calif., and the like.

Terms used herein should be accorded their ordinary meaning in the relevant arts, or the meaning indicated by their use in context, but if an express definition is provided, that meaning controls.

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Firmware" in this context refers to software logic embodied as processor-executable instructions stored in read-only memories or media.

"Hardware" in this context refers to logic embodied as analog or digital circuitry.

"Logic" in this context refers to machine memory circuits, non transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Software" in this context refers to logic implemented as processor-executable instructions in a machine memory (e.g. read/write volatile or nonvolatile memory or media).

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

Various logic functional operations described herein may be implemented in logic that is referred to using a noun or noun phrase reflecting said operation or function. For example, an association operation may be carried out by an "associator" or "correlator". Likewise, switching may be carried out by a "switch", selection by a "selector", and so on.

What is claimed is:

1. A method comprising:
receiving a rate of perceived exertion (RPE) through a user interface of a display device;
combining the RPE with a movement, a movement load, and movement repetitions into movement set data;
operating a dynamic exertion algorithm to:
generate a prescribed load and prescribed movement repetitions from a one repetition maximum load value, historical movement set data, a relative exertion model and a calibration and adjustment model, wherein the relative exertion model defines a relationship between the movement load, the movement repetitions, and the RPE, and the relative exertion model determines an expected RPE;

determine a difference in RPE from the expected RPE through operation of a comparator;
recalculate the one repetition maximum load value using the calibration and adjustment model when the difference in RPE is greater than an RPE threshold value; and
generate a display control comprising the prescribed load and the prescribed movement repetitions; and
displaying an adjusted movement information display comprising the prescribed load and the prescribed movement repetitions through the user interface, in response to configuration of a user interface controller with the display control.

2. The method of claim 1 further comprises:
operating the dynamic exertion algorithm further comprises:
generate the prescribed movement repetitions from a maximum repetitions value, the historical movement set data, a repetition-based relative exertion model and the calibration and adjustment model, wherein the repetition-based relative exertion model defines a relationship between the maximum repetitions value, the movement repetitions, and the RPE, and the repetition-based relative exertion model determines the expected RPE;
determine the difference in RPE from the expected RPE through operation of the comparator;
recalculate the maximum repetitions value using the calibration and adjustment model when the difference in RPE is greater than the RPE threshold value; and
generate the display control comprising the prescribed movement repetitions; and
displaying the adjusted movement information display comprising the prescribed movement repetitions through the user interface, in response to the configuration of the user interface controller with the display control.

3. The method of claim 1, wherein the adjusted movement information display comprises an RPE request in response to the user interface controller receiving an RPE request control with the display control.

4. The method of claim 3, wherein the RPE request control is generated by the dynamic exertion algorithm from the historical movement set data.

5. The method of claim 1, wherein the dynamic exertion algorithm generates the prescribed load and the prescribed movement repetitions from a related historical movement set data.

6. The method of claim 1, wherein receiving the RPE through the user interface of the display device is performed after each movement set.

7. The method of claim 1, wherein the receiving, combining, determining, operating, and displaying steps are performed after each movement set.

8. The method of claim 1, wherein a relative intensity adjustment algorithm recalculates the one repetition maximum load value when the difference in movement repetitions is greater than a movement repetition threshold value.

9. The method of claim 1, wherein the relative exertion model comprises expected RPE values charted against movement repetition values and completed intensity percentage values, wherein a particular expected RPE value corresponds to a particular completed intensity percentage value and a particular movement repetition value.

10. A computing apparatus comprising:
a processor; and
a memory storing instructions that, when executed by the processor, configure the apparatus to:
receive a rate of perceived exertion (RPE) through a user interface of a display device;
combine the RPE with a movement, a movement load, and movement repetitions into movement set data;
operate a dynamic exertion algorithm to:
generate a prescribed load and prescribed movement repetitions from a one repetition maximum load value, historical movement set data, a relative exertion model and a calibration and adjustment model, wherein the relative exertion model defines a relationship between the movement load, the movement repetitions, and the RPE, and the relative exertion model determines an expected RPE;
determine a difference in RPE from the expected RPE through operation of a comparator;
recalculate the one repetition maximum load value using the calibration and adjustment model when the difference in RPE is greater than an RPE threshold value; and
generate a display control comprising the prescribed load and the prescribed movement repetitions; and
display an adjusted movement information display comprising the prescribed load and the prescribed movement repetitions through the user interface, in response to configuration of a user interface controller with the display control.

11. The computing apparatus of claim 10, wherein the instructions further comprise:
operate the dynamic exertion algorithm to:
generate the prescribed movement repetitions from a maximum repetitions value, the historical movement set data, a repetition-based relative exertion model and the calibration and adjustment model, wherein the repetition-based relative exertion model defines a relationship between the maximum repetitions value, the movement repetitions, and the RPE, and the repetition-based relative exertion model determines the expected RPE;
determine the difference in RPE from the expected RPE through operation of the comparator;
recalculate the maximum repetitions value using the calibration and adjustment model when the difference in RPE is greater than the RPE threshold value; and
generate the display control comprising the prescribed movement repetitions; and
display the adjusted movement information display comprising the prescribed movement repetitions through the user interface, in response to the configuration of the user interface controller with the display control.

12. The computing apparatus of claim 10, wherein the adjusted movement information display comprises an RPE request in response to the user interface controller receiving an RPE request control with the display control.

13. The computing apparatus of claim 12, wherein the RPE request control is generated by the dynamic exertion algorithm from the historical movement set data.

14. The computing apparatus of claim 10, wherein the dynamic exertion algorithm generates the prescribed load and the prescribed movement repetitions from a related historical movement set data.

15. The computing apparatus of claim 10, wherein receiving the RPE through the user interface of the display device is performed after each movement set.

16. The computing apparatus of claim 10, wherein the receiving, combine, determining, operating, and displaying steps are performed after each movement set.

17. The computing apparatus of claim 10, wherein a relative intensity adjustment algorithm recalculates the one repetition maximum load value when the difference in movement repetitions is greater than a movement repetition threshold value.

18. The computing apparatus of claim 10, wherein the relative exertion model comprises expected RPE values charted against movement repetition values and completed intensity percentage values, wherein a particular expected RPE value corresponds to a particular completed intensity percentage value and a particular movement repetition value.

* * * * *